(12) United States Patent
Diehl et al.

(10) Patent No.: US 9,803,226 B2
(45) Date of Patent: Oct. 31, 2017

(54) EMULSION SYSTEMS AND EMULSION-BASED AMPLIFICATION OF NUCLEIC ACID

(71) Applicant: SYSMEX CORPORATION, Kobe-shi (JP)

(72) Inventors: Frank Diehl, Hamburg (DE); Philipp Angenendt, Hamburg (DE)

(73) Assignee: SYSMEX CORPORATION, Kobe-shi (JP)

(*) Notice: Subject to any disclaimer, the term of this patent is extended or adjusted under 35 U.S.C. 154(b) by 105 days.

(21) Appl. No.: 14/692,827

(22) Filed: Apr. 22, 2015

(65) Prior Publication Data

US 2015/0218609 A1 Aug. 6, 2015

Related U.S. Application Data

(63) Continuation of application No. PCT/IB2013/003084, filed on Oct. 28, 2013.

(60) Provisional application No. 61/719,175, filed on Oct. 26, 2012.

(51) Int. Cl.
*C12P 19/34* (2006.01)
*C12Q 1/68* (2006.01)

(52) U.S. Cl.
CPC ............ *C12P 19/34* (2013.01); *C12Q 1/6844* (2013.01)

(58) Field of Classification Search
CPC .............................. C12P 19/34; C12C 1/6844
USPC ........................ 436/6.1, 91.1; 435/6.1, 91.1
See application file for complete search history.

(56) References Cited

U.S. PATENT DOCUMENTS

| | | |
|---|---|---|
| 2004/0185484 A1 | 9/2004 | Costa et al. |
| 2006/0040297 A1* | 2/2006 | Leamon ............... B01L 3/5027 435/6.18 |
| 2010/0041048 A1 | 2/2010 | Diehl et al. |
| 2010/0190153 A1 | 7/2010 | Diehl et al. |
| 2011/0201526 A1 | 8/2011 | Berka et al. |
| 2012/0088684 A1 | 4/2012 | Liu |
| 2016/0194629 A1* | 7/2016 | Hinz ................... B01J 19/0046 506/2 |

FOREIGN PATENT DOCUMENTS

| | | |
|---|---|---|
| EP | 2 405 020 | 1/2012 |
| WO | WO 2005/073410 | 8/2005 |

OTHER PUBLICATIONS

Diehl et al., "BEAMing: single-molecule PCR on microparticles in water-in-oil emulsions," *Nature Methods*, 3(7):551-559, 2006.
Kojima et al., "PCR amplification from single DNA molecules on magnetic beads in emulsion: application for high-throughput screening of transcription factor targets," *Nucleic Acids Research*, 33(17):e150-e150, 2005.
Nakano et al., "Single-molecule PCR using water-in-oil emulsion," *Journal of Biotechnology*, 102(2):117-124, 2003.
PCT International Search Report and Written Opinion issued in International Patent Application No. PCT/IB2013/003084, dated May 12, 2014.
Saito et al., "Time-resolved tracking of a minimum gene expression system reconstituted in giant liposomes," *ChemBioChem*, 10(16):1640-1643, 2009.
Sjoblom et al., "Water-in-crude oil emulsions from the Norwegian continental shelf," *Colloid and Polymer Science*, 268:389-398, 1990.
Yamada et al., "Spontaneous transfer of phospholipid-coated oil-in-oil and water-in-oil micro-droplets through an oil/water interface," *Langmuir: The ACS Journal of Surfaces and Colloids*, 22:9824-9828, 2006.

* cited by examiner

*Primary Examiner* — Jezia Riley
(74) *Attorney, Agent, or Firm* — Parker Highlander PLLC (57) ABSTRACT

Methods for efficient and high throughput emulsion-based nucleic amplification are provided. In some aspects, emulsion mixtures are provided that require extremely low input energy (e.g., the energy generated by pipetting) to form emulsions that are effective for nucleic acid amplification. Efficient formulations for breaking emulsions are likewise provided.

17 Claims, 6 Drawing Sheets

EMULSION SYSTEMS AND EMULSION-BASED AMPLIFICATION OF NUCLEIC ACID

This application is a continuation of International Application No. PCT/IB2013/003084, filed Oct. 28, 2013, which claims priority to U.S. Provisional Patent Application No. 61/719,175, filed on Oct. 26, 2012. The entire contents of the above-referenced disclosures are specifically incorporated herein by reference.

The sequence listing that is contained in the file named "ISTCP0003US_ST25.txt", which is 1 KB (as measured in Microsoft Windows®) and was created on Jan. 21, 2015, is filed herewith by electronic submission and is incorporated by reference herein.

BACKGROUND OF THE INVENTION

1. Field of the Invention

The present invention relates generally to the field of chemistry and molecular biology. More particularly, it concerns emulsion formulations and methods for emulsion amplification of nucleic acid.

2. Description of Related Art

Emulsion PCR allows for the parallel analysis of millions of compartmentalized polynucleotide molecules within a single reaction vessel. BEAMing (beads, emulsions, amplification, and magnetics) built on emulsion PCR by keeping products formed within each compartment together once the emulsions are broken. This was accomplished through (i) inclusion of beads within the compartments and (ii) ensuring that at least one strand of the PCR product is bound to the beads. After amplification, each bead is coated with thousands of copies of the single DNA molecule present in the compartment that contained the bead and, after emulsion breaking, these beads could easily be recovered with a magnet or by centrifugation.

Beads obtained via BEAMing accurately reflect the polynucleotide diversity present in the template population and can be used to determine what fraction of a polynucleotide population contains a specific sequence variation. Because each bead contains thousands of molecules of the identical sequence, the signal to noise ratio obtained with methods to determine the polynucleotide sequence is extremely high. Millions of beads can be analyzed within minutes using conventional flow cytometry or sequencing instruments. However, conventional BEAMing techniques remain cumbersome and have not been successfully adapted for high throughput analyses. Thus, there remains a need for new emulsion reagents and techniques to address these issues.

SUMMARY OF THE INVENTION

In a first embodiment a method is provided for making an emulsion comprising: (a) providing a mixture comprising an aqueous phase and an oil mixture; and (b) emulsifying the mixture by passing the mixture through an orifice having a diameter between 2 mm and 50 µm with a velocity of 40 µl/s to 220 µl/s to generate an emulsion. In a related embodiment a method is provided for emulsion polymerase amplification comprising: (a) providing a mixture comprising an aqueous phase comprising polymerase reaction mixture and an oil mixture; (b) emulsifying the mixture by passing the mixture through an orifice having a diameter between 2 mm and 50 µm with a velocity of 40 µl/s to 220 µl/s; and (c) subjecting the emulsion to conditions sufficient for nucleic acid amplification. In some aspects, a method further involves (d) breaking the emulsion to separate the oil and aqueous phases (e.g., by additional breaking solution of the embodiments). In still a further aspect, a method can involve (e) removing the oil and/or aqueous phase after breaking the emulsion. In yet a further aspect, a method comprises (f) removing residual oil from an aqueous phase by addition of an emulsion clean-up solution. In still yet a further aspect, a method comprises (g) analyzing nucleic acid amplified in an emulsion of the embodiments (e.g., by sequencing or hybridization).

Certain aspects of the embodiments comprise emulsifying a mixture comprising an oil mixture and an aqueous phase (an emulsion mixture). In some aspects, emulsification comprises passing the emulsion mixture through an orifice to provide a sufficient input energy to generate an emulsion (e.g., an emulsion that can be used for nucleic acid amplification). For example, a mixture can be passed through an orifice with a velocity of 60 µl/s to 180 µl/s; 80 µl/s to 160 µl/s; or 80 µl/s to 120 µl/s (e.g., with a velocity of about 100 µl/s). An orifice for use according to the embodiments can in some aspects have a diameter of between about 1 mm and 100 µm; 800 µm and 200 µm; or 800 µm and 400 µm (e.g., a diameter of about 600 µm). Thus, in some aspects, the orifice is the orifice of a standard pipette tip.

In some aspects, passing the emulsion mixture through an orifice can comprise pipetting the mixture (e.g., passing the mixture up and down through a pipette tip repeatedly). Such pipetting can be performed manually or may be automated, such as by use of a computer controlled robot. In certain aspects, passing the emulsion mixture through an orifice comprises passing the mixture through the orifice at least 5, 10, 15, 20, 25, 30, 35 or 40 times. In some aspects, the emulsion mixture is passed through the orifice between 5 and 40 times, between 10 and 40 times or between 10 and 30 times (e.g., no more than 40 times).

In further aspects, one or more steps of a method of the embodiments is automated (e.g., using an automated liquid handling system). For example, in some cases, the emulsifying step; the nucleic acid amplification step; the emulsion breaking step; the aqueous/oil phase separation step; a bead separation step; a bead washing step; and/or nucleic acid analysis step may be automated.

In still further aspects, a method of the embodiments is further defined as a method for emulsion polymerase amplification in a plurality of reaction vessels (e.g., in 6, 12, 24, 48, 96 or more reaction vessels). For example, the plurality of reaction vessels can be arrayed as wells on a plate (e.g., a 96- or 384-well plate).

As described above, in some aspects, an aqueous phase or emulsion mixture of the embodiments comprises reagents for nucleic acid amplification. For example, the aqueous phase or emulsion mixture can comprise a DNA polymerase (e.g., a Taq DNA polymerase), primers, nucleotides, and/or template nucleic acids (e.g., DNA from a sample to be tested). In still further aspects, an emulsion mixture or an aqueous phase of the embodiments further comprises a plurality of beads (e.g., magnetic beads). In yet a further embodiment the plurality beads are linked to a nucleic acid molecule (e.g., a primer).

In certain aspects, a method of the embodiment comprises emulsifying an oil mixture with an aqueous phase. In some aspects, the oil mixture is one of the compositions detailed below, such as a composition comprising mineral oil, diethylhexyl carbonate, polyglyceryl-4 isostearate, cetyl PEG/PPG-10/1-dimethicone, hexyl laurate and/or polyglyceryl-3-oleate (e.g., an oil mixture comprising mineral oil, diethylhexyl carbonate, polyglyceryl-4 isostearate, cetyl PEG/PPG-10/1-dimethicone and hexyl laurate).

In a further embodiment an oil mixture is provided comprising (a) 10-30% (w/v) mineral oil; (b) 55-75% (w/v) diethylhexyl carbonate (e.g., Tegosoft® DEC); (d) 5-15% (w/v) of a composition consisting of polyglyceryl-4 isostearate; cetyl PEG/PPG-10/1-dimethicone; and hexyl laurate (e.g., ABIL® WE09); and (d) 5-15% (w/v) of a co-emulsifier of the embodiments (e.g., polyglyceryl-3-oleate or polyglyceryl-4 isostearate). For example, in some aspects, a co-emulsifier for use according to the embodiments comprises HLB value of between 3 to 8 and molecular weight of less than 10,000 g/mol. In a further aspect an oil mixture comprises: (a) 15-25% (w/v) mineral oil; (b) 60-70% (w/v) diethylhexyl carbonate; (d) 5-10% (w/v) of a composition consisting of polyglyceryl-4 isostearate; cetyl PEG/PPG-10/1-dimethicone; and hexyl laurate; and (d) 5-10% (w/v) of polyglyceryl-3-oleate or polyglyceryl-4 isostearate. For example, an oil mixture can comprise: (a) 18-22% (w/v) mineral oil; (b) 62-66% (w/v) diethylhexyl carbonate; (d) 5-10% (w/v) of a composition consisting of polyglyceryl-4 isostearate; cetyl PEG/PPG-10/1-dimethicone; and hexyl laurate; and (d) 5-10% (w/v) of polyglyceryl-3-oleate or polyglyceryl-4 isostearate.

In still yet a further embodiment there is provided an emulsion breaking solution (e.g., a solution that can be used to break-up an emulsion after nucleic acid amplification) comprising: (a) 20-50% 2-butanol; (b) 20-50% 1-propanol; and (c) 10-40% of water, wherein the solution comprises at least one detergent and at least one salt. In some specific aspects the emulsion breaking solution comprises: (a) 30-50% 2-butanol; (b) 30-50% 1-propanol; and (c) 10-30% of water. In some aspects, the solution comprises an anionic detergent, a non-ionic detergent, a cationic detergent or a zwitterionic detergent. In further aspects, an emulsion breaking solution can comprise 0.1% to 2.0% of an anionic detergent, such as sodium dodecyl sulfate (SDS). In still further aspects, the emulsion breaking solution comprises an alkaline denaturing agent (e.g., NaOH), for denaturing nucleic acid. Further components for an emulsion breaking solution include, without limitation, a pH buffering agent (e.g., TRIS or HEPES), one or more salts (e.g., NaCl), a nonionic detergent (e.g., Triton X-100), or a chelator (e.g., EDTA).

In a yet a further embodiment there is provided an emulsion clean-up solution (e.g., a solution that can be used for breaking-up an emulsion and/or removing residual oil from an aqueous phase after breaking of an emulsion). Such an emulsion clean-up solution can comprise: (a) 5-20% 2-butanol; (b) 5-20% 1-propanol; (c) 70-90% of water; at least one detergent and at least one salt. For example, the detergent can be an anionic detergent (e.g., SDS), a non-ionic detergent (e.g., Triton X-100), a cationic detergent or a zwitterionic detergent. In some aspects an emulsion cleanup solution further comprises one or more of a pH buffering agent, salt (e.g., NaCl), a chelator (e.g., EDTA), or an alkaline denaturing agent (e.g., NaOH).

Thus, in a further embodiment a method is provided for demulsification (i.e., breaking an emulsion) of an emulsion and for subsequent recovery of the beads. The demulsification method can comprise adding an emulsion breaking buffer of the embodiments to an emulsion, thereby breaking the emulsion. In some aspects, a demulsification method of the embodiments comprises pipetting an emulsion that comprises an emulsion breaking solution of the embodiments. In certain embodiments, the emulsion comprises beads and during the demulsification the beads are released from the aqueous compartments and separated from nucleic acid molecules which are not bound to beads. In further aspects, the beads can separated from the water and oil phase by centrifugation or magnetic collection (e.g., in the case of magnetic beads). In yet further aspects, the beads can be washed with a solution, such as an emulsion clean-up solution of the embodiments.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Invention

Recently developed techniques for emulsion-based amplification of a multitude of individual nucleic acid molecules have been demonstrated as a powerful new analytic method. The BEAMing technique built on emulsion PCR by keeping products formed within each compartment together once the emulsions are broken. Thus, beads obtained via BEAMing accurately reflect the polynucleotide diversity present in the template population and can be used, e.g., to determine what fraction of a polynucleotide population contains a specific sequence variation. However, while state of the art BEAMing methods are effective for DNA amplification they are less than amendable to scale-up for standardizable high throughput techniques that can leverage the true power of BEAMing. For example, emulsions for use in nucleic acid amplification have required high amounts of input energy to generate an effective emulsion, and thus specialized machines are required to generate each emulsion systems.

The method and reagents detailed here overcome the limitations of previous emulsion amplification techniques by providing a system that requires only a low amount of input energy to generate an emulsion effective for nucleic acid amplification and which is amenable to high throughput assay systems. In particular, systems that include a co-emulsifier have been identified that reduce the emulsion energy of the system, such that pipetting alone can be used to generate a robust emulsion. Thus, the method and reagents described here provide for easier formation of homogenous populations of water-in-oil emulsions that allow a transfer-free subsequent PCR amplification. Moreover, the use of new formulations for demulsification allow for a transfer-free, efficient, recovery of the beads. The new methods provided here can therefore be used to complete high throughput, highly reproducible, nucleic acid analyses by BEAMing.

II. Emulsion Mixtures and Modification of Emulsions

For nucleic acid amplification in an emulsion, an emulsion reaction is typically created by vigorously shaking or stirring a "water in oil" mix to thereby applying sufficient input energy generate a multitude of micron-sized aqueous compartments. According to one embodiment, the invention provides a method for generation of a water-in-oil emulsion using a reduced input energy, such as that can be achieved by pipetting of an emulsion mixture. Emulsions comprising aqueous compartments in a continuous oil phase (water-in-oil emulsion) are formed using a pipette tip and repeated pipetting cycles. The aqueous phase comprises one or more species of a polynucleotide templates, beads, enzymes, salts, buffers, and oligonucleotide primers, for amplifying said template. The number of separate emulsion populations that can be formed in parallel is increased using multi-well plates.

The nucleic acid and/or beads are mixed in a limiting dilution to generate compartments containing, on average, just one nucleic acid molecule and/or bead (at the optimal dilution many compartments may be empty). In some cases to facilitate amplification efficiency, both an upstream (low concentration, matches primer sequence on bead) and downstream nucleic acid primers (high concentration) are included in the reaction mix. Depending on the size of the aqueous compartments generated during the emulsification step, $3\times10^9$ or even more individual amplification reactions per μl can be conducted simultaneously in the same tube. Essentially each compartment in the emulsion forms a micro PCR reactor. The average size of a compartment in an emulsion ranges from sub-micron in diameter to over 100 microns, depending on the emulsification conditions. For example, the compartment may have a diameter of 0.5 to 50 microns. In further aspects, the compartments may be from 1 to 10 microns, inclusive, from 11 to 100 microns, inclusive, or about 5 microns, on average. The preferred compartment size will vary depending upon the precise requirements of an assay that is to be performed according to the present embodiments. Compartment size, for instance, can be adjusted depending of the size bead that is used. In the case of a 1 μm bead, compartments of 5-10 μm may be preferred.

In certain aspects, a portion of the compartments of an emulsion comprise a bead (e.g., a bead with an attached oligonucleotide). All such compartments need not comprise a bead. Desirably, at least one in 10,000 of said aqueous compartments comprise a bead. Typically from 1/100 to 1/1 or from 1/50 to 1/1 of said aqueous compartments comprise a bead. Preferably and emulsion comprises 1 bead per compartment. In particular, in order to allow amplification of single molecules on beads it is desired to have fewer DNA molecules than beads such that each aqueous compartment contain no more than 1 bead.

As used herein the term "emulsion mixture" refers to a mixture of an oil and aqueous phase. An emulsion mixture may comprise separated phases or may be emulsified. Certain emulsion mixtures for use in nucleic acid amplification and for BEAMing have been previously described. Exemplary emulsion mixtures are provided for example in U.S. Patent Publns. 20120088684; 20110201526 and 20100190153, each of which is incorporated herein by reference in its entirety. These mixtures prove effective for DNA amplification but require specialized mechanical devices, such as, homogenizes, colloid mills, or "membrane emulsification" devices for effective emulsification (Becher, 1957; Dickinson, 1994). On the other hand, oil mixtures of the embodiments comprise an additional co-emulsifier that lower the activation energy for emulsification. Thus, emulsion mixtures of the embodiments comprise lower activation energy (for emulsification), while maintaining robust and properly sized compartments for nucleic acid separation once an emulsion is formed.

In general, water-in-oil emulsions are formed from heterogeneous systems of two immiscible liquid phases with one of the phases dispersed in the other as droplets of microscopic or colloidal size (Becher, 1957; Sherman, 1968; Lissant, 1974; Lissant, 1984). Emulsions may be produced from any suitable combination of immiscible liquids. Preferably the emulsion of the present embodiments has water that contains the biochemical components, as the phase present in the form of finely divided microcapsules (the disperse, internal or discontinuous phase) and a hydrophobic, immiscible liquid (an "oil", such as mineral oil) as the matrix in which these microcapsules are suspended (the nondisperse, continuous or external phase). This has the advantage that the entire aqueous phase containing the biochemical components is compartmentalized in discreet microcapsules (the internal phase). The hydrophobic oil phase, generally contains none of the biochemical components and hence is inert.

The primary emulsion may be stabilized by addition of one or more emulsifying agents and act at the water/oil interface to prevent (or at least delay) separation of the phases. Many oils and many emulsifiers can be used for the generation of water-in-oil emulsions; a recent compilation listed over 16,000 compounds, many of which are used as emulsifying agents (Ash and Ash, 1993, incorporated herein by reference). Particularly suitable oils include light white mineral oil and non-ionic emulsifying agents (Schick, 1966)

such as sorbitan monooleate (Span™80; ICI), octyl phenol ethoxylate (Triton™ X-100) and polyoxyethylenesorbitan monooleate (Tween™80; ICI). Other emulsifying agents that may be used include, without limitation, silicone-based emulsifier such as Bis-PEG/PPG-14/14 Dimethicone, Cyclopentasiloxane (ABIL™ EM 90) or ABIL® WE09.

Water-in-oil emulsions of the present embodiments are generally stable with little if any exchange of contents (e.g., nucleic acids) between the compartments in the emulsion. Additionally, biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of liters (Becher, 1957; Sherman, 1968; Lissant, 1974; Lissant, 1984).

The aqueous phase in an emulsions of the embodiments typically comprises at least 10, 15, 20, 25, 35 or 35, and up to 40% (v/v) of the emulsion. Accordingly, the oil phase typically comprises at least 60, 65, 70, 75, 80, or 85, and up to 90% (v/v) of emulsions. The emulsifier (or mixture of emulsifiers), although amphiphilic, is considered part of the oil phase. It is believed to align at the interface of the two phases upon formation of an emulsion. Hydrocarbons which form the oil phase are typically oils or waxes and can be characterized by their viscosities. For example, oil compositions or emulsion mixtures can have a dynamic viscosity of <5 mPa·s (very low viscosity); 5-10 mPa·s (low viscosity); 10-20 mPa·s (medium viscosity); 20-50 mPa·s (high viscosity); or >50 mPa·s (very high viscosity) (all viscosity measurements are based on room temperature, 25° C. assay conditions).

A lower viscosity oil (defined as a very low, low, and/or medium) is easier to work with than a high viscosity oil. The low viscosity oil can have a viscosity of less than 10 or less than 5 mPas at 25° C. A high viscosity oil can be within a range of 10-30, 20-25, or 22-26 mPas at 25° C. The majority of the oil phase can be either a very low, a low, a medium, or a mixture of such oils or waxes. The proportion of lower viscosity oil to high viscosity oil can vary from 85:10 to 60:30. At least 60, 65, 70, 75, or 80 and up to 85% (v/v) of the oil phase can be a lower viscosity oil. At least 10, 15, 17, 20, or 25, and up to 23, 25, 27, or 30% (v/v) of the oil phase can be a high viscosity oil. The emulsifier can comprise at least 5, 6, 7, 8, or 9% and up to 10% (v/v) of the oil phase.

In some aspects an emulsifier or co-emulsifier of the embodiments may be characterized according to a Hydrophile-Lipophile Balance (HLB) value, which is a measure of the molecule's (or compositions's) hydrophilicity compared to its lipophilicity. HLB values range from 0-60 and define the relative affinity of a surfactant for water and oil. Nonionic molecules generally have HLB values ranging from 0-20 and ionic molecules may have HLB values of up to 60. Hydrophilic emulsifiers have HLB values greater than about 10 and a greater affinity for water than oil. Lipophilic emulsifiers and co-emulsifiers are preferred in certain aspects and have HLB values less than about 10 and a greater affinity for oil than water.

Co-Emulsifiers

In certain aspects, a co-emulsifier is employed in an emulsion mixture of the embodiments. The co-emulsifier functions to lower the total input energy that is required to form an emulsions that can function efficiently for, e.g., emulsion PCR (emPCR). A co-emulsifiers can act together with the other emulsifiers in a mixture to facilitate the formation and stabilization of the aqueous compartments in the emulsion. In some aspects, a co-emulsifier for use according the embodiments comprises a HLB value of between about 3 and about 8. In further aspects, a co-emulsifier selected for us according to the embodiments comprises a molecular weight of <10,000 g/mol. Examples of co-emulsifiers for use according to embodiments include, with limitation, polyglyceryl-3-oleate or polyglyceryl-4 isostearate. An example oil mixture including a co-emulsifier of the embodiments is illustrated in Table 1 below.

TABLE 1

Example oil mixture of the embodiments.

| Name | Supplier | Cat# | CAS No. | Conc. |
|---|---|---|---|---|
| ABIL ® WE09 (Polyglyceryl-4 isostearate; Cetyl PEG/PPG-10 1-Dimethicone; Hexyl laurate) | Evonik | FC20132171K | 91824-88-3 144243-53-8 34316-64-8 | 7.9% (w/w) |
| Isolan ® GO33 (Polyglyceryl-3-oleate) | Evonik | FC20065371K | 33940-98-6 | 7.9% (w/w) |
| Tegosoft ® DEC (Diethylhexyl Carbonate Or Carbonic Acid, Bis(2-Ethylhexyl) Ester) | Evonik | FC20579871 | 14858-73-2 | 64.0% (w/w) |
| Mineral Oil | Sigma Aldrich | M3516 | 8042-47-5 | 20.3% (w/w) |

De-Emulsification and Emulsion Clean-Up

Emulsions of the embodiments can be "broken" or disrupted by any means known in the art. One particularly simple way to break the emulsions is to add more detergent. Detergents which can be used include, but are not limited to Triton X100, Laureth 4 and Nonidet (e.g., NP-40). Preferably, an emulsion breaking solution not only provides effective phase separation, but also prevents clumping of beads released from an emulsion. The emulsion breaking buffer also prevents the formation of an oil phase, which is not easily removable by pipetting. As exemplified herein it has been found that additional certain alcohols to the breaking solution can greatly enhance emulsion breaking, while keeping bead clumping to a minimum and allow pipetting. For example, in some aspects, an emulsion breaking solution comprises 2-butanol and/or 1-propanol. An example, formulation for an emulsion breaking solution of the embodiments is shown in Table 2 below.

TABLE 2

Example emulsion breaking solution.

| Name | Supplier | Cat# | CAS No. | Conc. |
|---|---|---|---|---|
| Sodium chloride | AppliChem | A7006 | 7647-14-5 | 25 mM |
| Triton X-100 (Polyethylene glycol p-(1,1,3,3-tetramethylbutyl)-phenyl ether, octyl phenol ethoxylate or polyoxyethylene octyl phenyl ether) | Sigma-Aldrich | T8787 | 9002-93-1 | 0.25% (v/v) |

TABLE 2-continued

Example emulsion breaking solution.

| Name | Supplier | Cat# | CAS No. | Conc. |
|---|---|---|---|---|
| Tris-HCl (pH 7.5) (2-Amino-2-hydroxymethyl-propane-1,3-diol hydrochloride or Tris(hydroxymethyl)aminomethane hydro chloride) | AppliChem | A4263 | 1185-53-1 | 2.5 mM |
| EDTA (Ethylenediaminetetraacetic acid) | AppliChem | A3145 | 60-00-4 | 0.25 mM |
| SDS (Sodium dodecyl sulfate) | AppliChem | A3942 | 151-21-3 | 0.5% (v/v) |
| 2-Butanol | Sigma-Aldrich | B85919 | 78-92-2 | 40% (v/v) |
| 1-Propanol | Sigma-Aldrich | 538000 | 71-23-8 | 35% (v/v) |
| Water | AppliChem | A1991 | 7732-18-5 | 24.25% (v/v) |

In some aspects, an emulsion breaking solution may also be used to further clean-up a reaction, such as by wash residual oil from beads and/or a reaction vessel. Likewise, in some aspects, an emulsion clean-up solution can be used for washing of beads and/or for nucleic acid denaturation. In some aspects, an emulsion clean-up solution comprises 2-butanol and/or 1-propanol. An example, formulation for an emulsion clean-up solution of the embodiments is shown in Table 3 below.

TABLE 3

Example emulsion clean-up solution.

| Name | Supplier | Cat# | CAS No. | Conc. |
|---|---|---|---|---|
| Sodium chloride | AppliChem | A7006 | 7647-14-5 | 80 mM |
| Triton X-100 (Polyethylene glycol p-(1,1,3,3-tetramethylbutyl)-phenyl ether, octyl phenol ethoxylate or polyoxyethylene octyl phenyl ether) | Sigma-Aldrich | T8787 | 9002-93-1 | 0.8% (v/v) |
| EDTA (Ethylenediaminetetraacetic acid) | AppliChem | A3145 | 60-00-4 | 0.8 mM |
| SDS (Sodium dodecyl sulfate) | AppliChem | A3942 | 151-21-3 | 0.8% (v/v) |
| Sodium hydroxide | AppliChem | A1432 | 1310-73-2 | 80 mM |
| 2-Butanol | Sigma-Aldrich | B85919 | 78-92-2 | 10% (v/v) |
| 1-Propanol | Sigma-Aldrich | 538000 | 71-23-8 | 10% (v/v) |
| Water (p.A.) | AppliChem | A1991 | 7732-18-5 | 78.4% (v/v) |

III. Nucleic Acid Amplification and Analysis

A general method for nucleic acid amplification and analysis according to the embodiments is provide e.g., in Diehl et al., 2006 and in U.S. Pat. Publn. 20100041048 each of which are incorporated herein by reference.

Samples which may be used as sources of analyte DNA (for analysis according to the embodiments) include blood, plasma, serum, urine, stool, sputum, tears, saliva, lavages, bone marrow or other bodily fluids. Solid tissues can also provide analyte DNA. Samples can be from tissues believed to healthy or from disease tissues (e.g., tumors). Samples can be obtained from diseased individuals (e.g., cancer patients), from related family members, from pregnant women, and from neonates. Sources of analyte DNA may be treated, for example with test agents, and the effects of the test agents on the analyte DNA can be determined.

Sample DNA for amplification and analysis according to the present invention can be genomic DNA, cDNA, PCR products of genomic DNA, or PCR products of cDNA, for example. Samples can be derived from a single individual, for example, from a body sample such as urine, blood, sputum, stool, tissue or saliva. Samples can also be derived from a population of individuals. The individuals can be humans, but can be any organism, plant or animal, eukaryotic or prokaryotic, viral or non-viral.

After amplification, product beads can be analyzed to determine a sequence feature of the DNA bound to them. Any method for determining a sequence feature can be used, including, hybridization, primer extension, and nucleotide sequencing. In some cases, product beads can be analyzed by flow cytometry, i.e., a technique for separating or distinguishing different species of nucleotide molecule or fluorescently labeled beads. Other means of analysis can be used as is convenient.

Beads for use according to the present embodiments can vary between about 0.1 and 10 microns in diameter. Typically beads are made of a polymeric material, such as polystyrene, although nonpolymeric materials such as silica can also be used. Other materials which can be used include styrene copolymers, methyl methacrylate, functionalized polystyrene, glass, silicon, and carboxylate. Optionally the particles are superparamagnetic, which facilitates their purification after being used in reactions.

Beads can be modified by covalent or non-covalent interactions with other materials, either to alter gross surface properties, such as hydrophobicity or hydrophilicity, or to attach molecules that impart binding specificity. Such molecules include without limitation, antibodies, ligands, members of a specific-binding protein pair, receptors, nucleic acids or chemically active groups (e.g., an aldehyde or carboxy group). Specific-binding protein pairs include avidin-biotin, streptavidin-biotin, and Factor VII-Tissue Factor.

Oligonucleotide primers can be bound to beads by any means known in the art. They can be bound covalently or non-covalently. They can be bound via an intermediary, such as via a protein-protein interaction, such as an antibody-antigen interaction or a biotin-avidin interaction. Other specific binding pairs as are known in the art can be used as well. To achieve optimum amplification, primers bound to the bead may be longer than necessary in a homogeneous, liquid phase reaction. Oligonucleotide primers may be at least 12, at least 15, at least 18, at least 25, at least 35, or at least 45 nucleotides in length. The length of the oligonucleotide primers which are bound to the beads need not be identical to that of the primers that are in the liquid phase. Primers can be used in any type of amplification reaction known in the art, including without limitation, polymerase chain reaction, isothermal amplification, rolling circle amplification, self-sustaining sequence replication (3SR), nucleic acid sequence-based amplification (NASBA), transcription-mediated amplification (TMA), strand-displacement amplification (SDA), and ligase chain reaction (LCR).

Beads, after being prepared according to the present embodiments as product beads (i.e., after nucleic acid amplification), have more than one copy of the same nucleic acid molecule bound to them. Preferably each bead is bound to at least 100, 500, 1000, 10,000, 20,000 or more molecules of the same nucleic acid sequence. In some circumstances some of the product beads are bound to more than one type of nucleic acid molecule. These product beads are generally less useful in the analysis of ratios of genetic sequences in a population of genetic sequences.

Desirably, a substantial proportion of the product beads comprise only one type of nucleic acid per bead. A substantial proportion can be for example, at least 1%, at least 5%, at least 10%, or at least 50%. A population of product beads could also comprise two or more types of nucleic acids. Such a population is heterogeneous with respect to the nucleic acids. A product bead with only one type of nucleic acid per bead is termed homogeneous. Homogeneous beads with only one type of nucleic acid per bead include those with nucleic acids containing errors due to errors in polymerase chain reaction. A product bead with two types of nucleic acid per bead is termed heterogeneous. Although not wishing to be bound by any particular theory, heterogeneous product beads are thought to result from aqueous compartments which have more than two molecules of template of non-identical sequence. A population of product beads can be heterogeneous as a population but contain individual product beads that are homogeneous Populations of product beads can be maintained in a liquid suspension. Alternatively they can be sedimented and dried. The latter alternatives may be beneficial for storage stability.

Analysis of populations of product beads can be useful for distinguishing between many kinds of genetic variants. Polynucleotides can be distinguished which differ by as little as a single nucleotide polymorphism (SNP), by the presence or absence of a mutation, by the presence or absence of an insertion or deletion, by the presence or absence of a non-single nucleotide polymorphism. Thus populations of product beads may be heterogeneous with regard to these genetic variations.

One very convenient way for distinguishing genetic variants, i.e., determining a sequence feature of the analyte, is by differentially labeling the variants with fluorescent dyes. Such labeling can be accomplished by hybridization of a fluorescently labeled oligonucleotide probe to one species of polynucleotide. Alternatively, a fluorescently labeled antibody can be used to specifically attach to one oligonucleotide probe that hybridizes to a particular genetic variant. Such antibody binding can be, for example, mediated by a protein or polypeptide which is attached to an oligonucleotide hybridization probe. Of course, other means of labeling polynucleotides as are known in the art can be used without limitation. Another means of labeling different polynucleotide species is by primer extension. Primers can be extended using labeled deoxyribonucleotides, such as fluorescently labeled deoxyribonucleotides.

Populations of product beads can be used as templates. Template analyte molecules on the product beads can be analyzed to assess DNA sequence variations by hybridization, primer-extension methods, ligation, enzymatic digestion, and other methods commonly used in the art. Template analyte molecules on product beads can be employed for sequencing. In one sequencing technique, product beads are arrayed by placing them on slides spotted with complementary oligonucleotides. In another sequencing technique, product beads are placed into individual wells. In still another sequencing technique product beads are incorporated into acrylamide matrices (with or without subsequent polony formation). Sequencing reactions can be performed with any method, such as those using unlabeled nucleotide precursors (e.g., pyrosequencing, as described in Ronaghi et al., 1999) or labeled nucleotides (e.g., photocleavable reagents described by Mitra et al., 003). Product beads can thus be used for and facilitate multiple parallel sequencing. Product beads can also be used in sequencing employing Type RS restriction endonucleases. Product beads can also be used to provide templates for conventional dideoxynucleotide sequencing. To obtain useful data upon sequence analysis, individual product beads, that are homogenous with templates are desirable. To provide a homogenous template population, product beads can be diluted, separated, or otherwise isolated so that each sequencing reaction contains a single product bead. Alternatively, product beads can be sorted to provide populations of beads with a single species of template.

Detailed methods for analysis of product beads and nucleic acids, such as by allele-specific hybridization (ASH), see e.g., U.S. Pat. Publn. 20100041048, incorporated herein by reference.

Amplicons can be any size which is efficiently amplified using polymerase chain reaction. In the case of templates obtained from a patient sample (e.g., a blood or serum sample), amplicons are preferably shorter than or equal to 300 bp, or shorter than or equal to 200 bp, or shorter than or equal to 100 bp.

Another optional step for improving the specificity and/or sensitivity of the allele discrimination reaction is to denature the double stranded nucleic acid duplexes attached to the beads prior to the hybridization reaction. For example, the double strands can be heated or treated with sodium hydroxide. After the separation of the two strands, the single strands which are not bound to the beads can be separated from the beads and the bead-bound strands, and the single strands can be discarded.

If desired, yet another step of amplification can be used after the emulsions are broken. This step typically employs isothermal amplification, also known as rolling circle amplification. In order to generate the rolling circle, a molecular inversion probe or a padlock probe can be used. They probe may require filling-in, or not, prior to a template-driven ligation reaction to generate a circle. If filling-in is required the region to be filled in will typically be from 1 to 30 nucleotides. The isothermal amplification can amplify the ultimately detected signal quite significantly. After isothermal amplification, a sequence feature can be detected using single base extension (SBE) or allele ASH reaction, as described above. Alternatively, the nucleotide sequence of the amplicon on the beads can be determined by any allele discrimination sequencing method known in the art, including sequencing-by-synthesis.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Emulsifier-Oil Mixture

Testing of standard pipette tips with the emulsifier-oil mixture. A series of tests was performed with variable numbers of pipetting cycles and variable concentrations of ABIL WE09. Emulsion PCR and oligonucleotide hybridization were performed to functionally test this approach. For these experiments, a single-channel pipette (20-200 μL; Cat# L-200XLS Mettler-Toledo, Rainin) and GP-L200F pipette tips (Rainin/Mettler-Toledo) were used to mix 18 μL of PCR mix with 62 μL of an emulsifier-oil mixture (6.5%, 7%, 7.5%, 8%, or 9% (w/v) ABIL WE09, 75% (w/v) Tegosoft DEC, and 18.5% (w/v) mineral oil). Mixing was performed by pipetting a 50 μL volume up and down 30-40 times. PCR cycling was performed as described in Example 3 using a PCR product with BEAMing sequence tags with a 2% mutation frequency for PIK3CA Ex9 1634 a>c. Emulsion breaking was performed with the newly developed breaking solutions 1 and 2 (see Example 2). Subsequent hybridization was performed as described in Example 3.

Thirty cycles consistently resulted in the formation of a bead precipitate on the bottom of the tube, which is the result of an excess of large aqueous compartments. Forty cycles did not produce a precipitate. The concentration of ABIL WE09 had no effect on the measured mutation fraction (average detected mutant fraction was 1.5% compared to an input of 2%). Therefore, standard pipette tips can be used to create emulsions for emulsion PCR applications (e.g., BEAMing).

The Generation of Emulsions with Fewer Pipetting Cycles (i.e., Less Energy Input) with the Use of Co-Emulsifiers.

The inventor screened commonly used emulsifiers by adding them to the standard emulsifier-oil mixture with or without ABIL WE09. The selection of co-emulsifiers was based on the HLB value (range of 3-8) and molecular weight (<10,000 g/mol). The experimental emulsifiers were prepared as follows: 0.18 g Emulgator (Isolan GO33, Isolan GI34, Isolan GPS, Isolan PDI, or Tegin OV), 0.35 g ABIL WE09 (for samples without ABIL WE09, mineral oil was substituted), 3.65 mL Tegosoft DEC, and 1 mL mineral oil. Alcohols were also tested for the ability to act as co-emulsifiers as follows: 0.35 g alcohol (1-octanol, 1-octyl-1-dodecanol, 1-haptoanol, 2-hexyl-1-deconal, or 1-nonanol), 0.35 g ABIL WE09, 3.65 mL Tegosoft DEC, and 1 mL mineral oil. A single-channel pipette (20-200 μl; Cat# L-200XLS Mettler-Toledo, Rainin) and GP-L200F pipette tips (Rainin/Mettler-Toledo) were used to mix 18 μL of PCR mix with 62 μL of an emulsifier-oil mixture. Mixing was performed by pipetting a 50 μL volume up and down 20 or 40 times. Emulsions were evaluated under an inverted microscope, head stability was assessed after amplification, and functional testing was performed in a subsequent BEAMing assay. PCR cycling was performed as described in Example 3 using a PCR product with BEAMing sequence tags with a 2% mutation frequency for PIK3CA Ex9 1634 a>c. Emulsion breaking was performed with the newly developed breaking solutions 1 and 2 (see Example 2). Subsequent hybridization was performed as described in Example 3.

Figure 1:
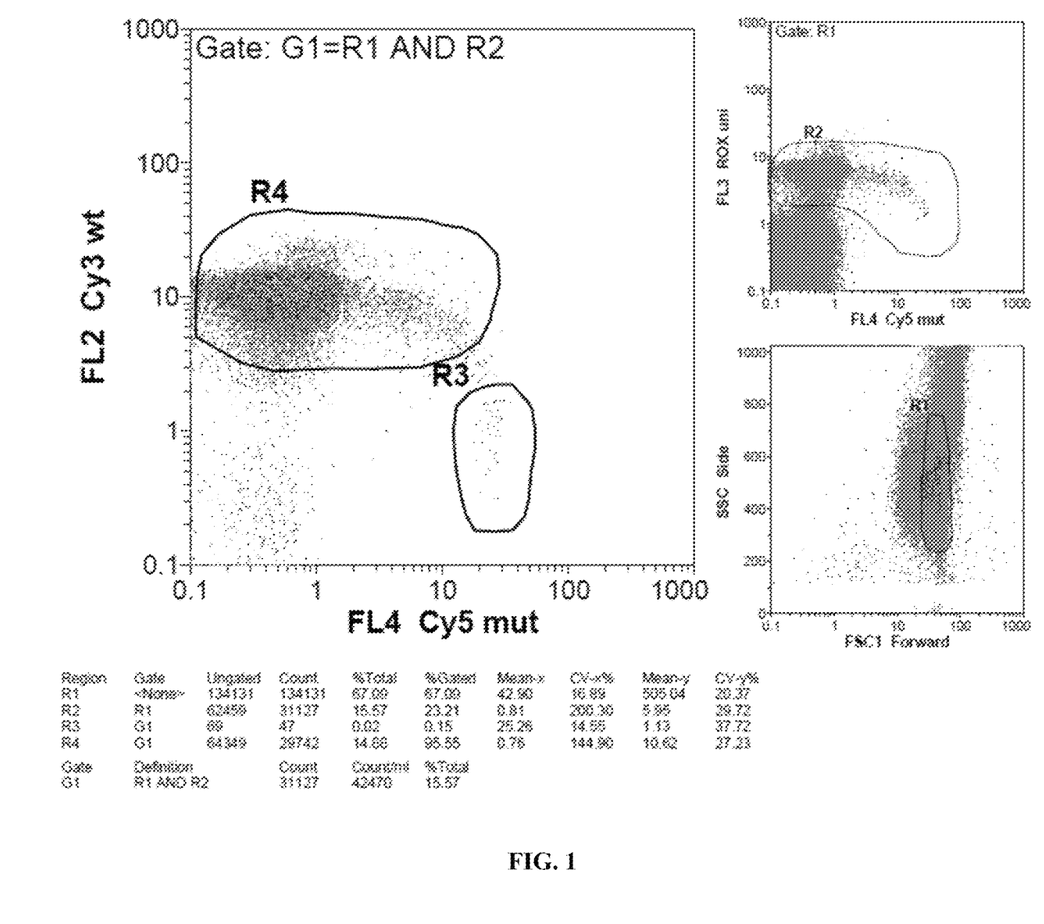
FIG. 1: Flow cytometry analysis of BEAMing beads generated by the Isolan GI34+ABIL WE09 mixture and 20× pipetting. The lower right panel shows the single bead population in the gate R1. The upper right panel shows beads that have been hybridized with a universal probe in gate R2. The left panel shows the single bead population of the minority (i.e., mutant) bead population in gate R3 and the majority (i.e., wild-type) in R4.
Figure 2:
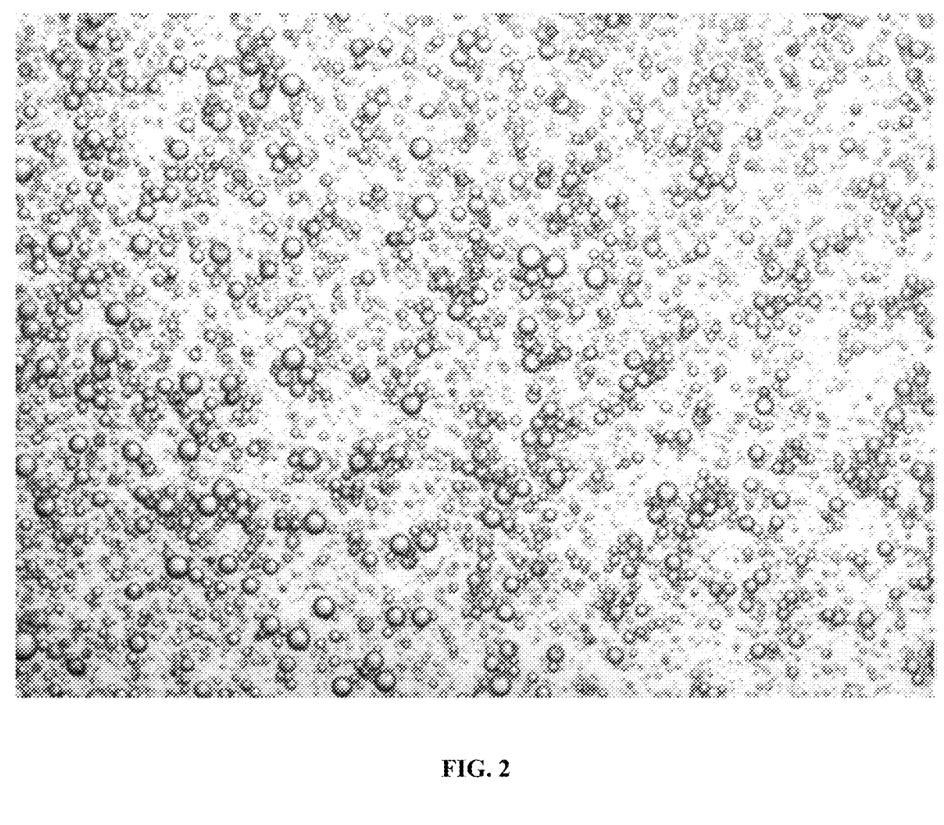
FIG. 2: Microscopic image (400×; phase contrast) of an emulsion prepared by 20× pipetting of the Isolan GI34+ABIL WE09 mixture. The emulsion was deposited for imaging on a standard tissue culture plate.

Data for the results of the alcohol co-emulsions are presented in Table 4. Due to the results of the microscopic evaluation, no further emulsion PCR amplification was performed using these co-emulsions. Data for the Emulgator co-emulsions are presented in Table 5. Two co-emulsifiers (Isolan GO33 and GI34) yielded positive results in the functional testing (FIG. 1). However, these co-emulsifiers only produced stable emulsions when combined with ABIL WE09. Additionally, 20× pipetting was sufficient to generate uniform water-in-oil emulsions (FIG. 2).

TABLE 4

Alcohol co-emulsions

| No. | Alcohol | 20x pipetting | 40x pipetting |
|---|---|---|---|
| 1 | 1-Octanol | Large − | Small + |
| 2 | 1-Octyl-1-dodecanol | Some large − | Small ++ |
| 3 | 1-Heptoanol | Some large − | Small ++ |
| 4 | 2-Hexyl-1decanol | Large − | Large − |
| 5 | 1-Nonanol | Large − | Small + |

TABLE 5

Emulgator co-emulsions.

| | | 20x pipetting (row A) | | | 40x pipetting (row B) | | |
|---|---|---|---|---|---|---|---|
| No # | Name | Microscope | Head Stability | PCR Result | Microscope | Head Stability | PCR Result |
| 1 | Isolan GO33 + ABIL WE 09 | NA | NA | Works | +++ | + | Works |
| 2 | Isolan GI34 + ABIL WE 09 | ++ | NA | Works | ++ | + | Works |
| 3 | Isolan GPS + ABIL WE 09 | + | NA | Bad | + | + | Bad |
| 4 | Isolan PDI + ABIL WE 09 | NA | NA | Bad | + | + | Bad |
| 5 | Tegin OV + ABIL WE 09 | NA | NA | Bad | ++ | + | Bad |
| 6 | Only ABIL WE 09 | − | NA | Bad | + | + | Works |
| 7 | Isolan GO33 no ABIL WE 09 | −− (burst) | NA | Works | −− (burst) | + | Works (+) |
| 8 | Isolan GI34 no ABIL WE 09 | −− (burst) | NA | Works | −− (burst) | + | Works |
| 9 | Isolan GPS no ABIL WE 09 | −− (beads sticky) | NA | Bad | −− (beads sticky) | + | Bad |

TABLE 5-continued

Emulgator co-emulsions.

| | | 20x pipetting (row A) | | | 40x pipetting (row B) | | |
|---|---|---|---|---|---|---|---|
| No # | Name | Microscope | Head Stability | PCR Result | Microscope | Head Stability | PCR Result |
| 10 | Isolan PDI no ABIL WE 09 | -- (beads sticky) | NA | bad | -- (beads sticky) | + | bad |

NA—not analyzed

Optimization of the Concentration of Co-Emulsifier (Isolan GO33 and GI34)-Oil Mixture.

A range of co-emulsifier concentrations was tested, including 1%, 2%, 2.5%, 3%, 3.5%, 4%, 5%, 6%, and 7%. A single-channel pipette (20-200 µL; Cat# L-200XLS Mettler-Toledo, Rainin) and GP-L200F pipette tips (Rainin/Mettler-Toledo) were used to mix 20 µL of PCR mix with 60 µL of an emulsifier-oil mixture. Mixing was performed by pipetting a 60 µL volume up and down 20 or 40 times. Co-emulsifier concentrations greater than 4% (preferably 7%) produced a positive visible effect.

Optimization of the Number of Pipetting Cycles.

A single-channel pipette (20-200 µL; Cat# L-200XLS Mettler-Toledo, Rainin) and GP-L200F pipette tips (Rainin/Mettler-Toledo) were used to mix 20 µL of PCR mix with 60 µL of an emulsifier-oil mixture comprising 5% of a co-emulsifier. Mixing was performed by pipetting a 60 µL volume up and down 10, 15, 20, 25, 30, 35, 40, or 45 times. At least 20 pipetting cycles were needed for optimal results and more than 35 had no additional effect. Therefore, the optimal range of pipetting cycles is 25-35 with the preferred number of mixing cycles being 30.

Optimization of the Ratio of Aqueous to Oil Phase.

A single-channel pipette (20-200 µL; Cat# L-200XLS Mettler-Toledo, Rainin) and GP-L200F pipette tips (Rainin/Mettler-Toledo) were used to mix 20 µL of PCR mix with either 60 or 70 µL of an emulsifier-oil mixture comprising 7% of a co-emulsifier (for a 1:4 and 1:4.5 ratio, respectively). Mixing was performed by pipetting a 60 µL volume up and down 20, 25, 30, or 35 times. Both aqueous-to-oil-phase ratios resulted in good emulsions with the preferred ratio being 1:4.5.

Optimization of the Mixing Volume.

A single-channel pipette (20-200 µL; Cat# L-200XLS Mettler-Toledo, Rainin) and GP-L200F pipette tips (Rainin/Mettler-Toledo) were used to mix 20 µL of PCR mix with 70 µL of an emulsifier-oil mixture comprising 7% of a co-emulsifier. Mixing was performed by pipetting either a 50, 60, 70, 80, or 90 µL volume up and down 30 times. Pipetting volumes greater than 80 uL resulted in too much air being in the pipette. The optimal mixing volume was 70 µL.

Testing of Different Pipette Tips and Pipette Types.

Figure 3:
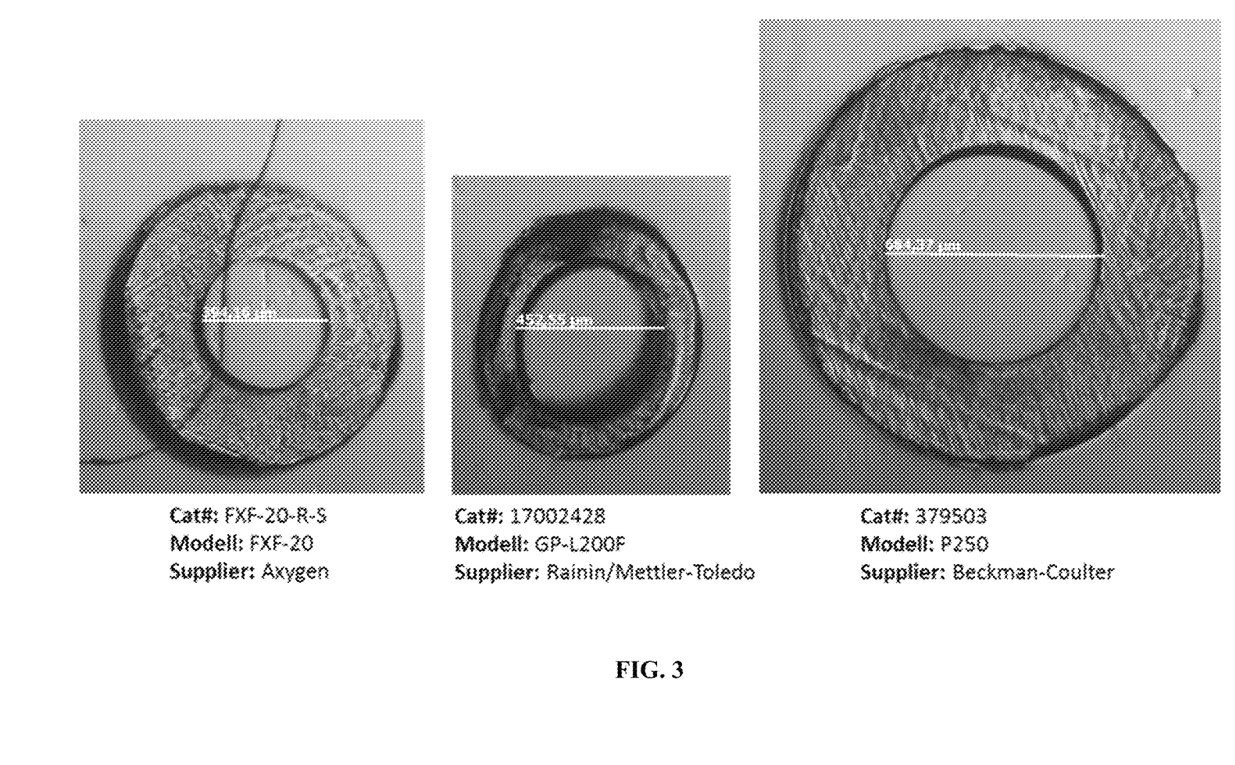
FIG. 3: Microscopic images pipette tip openings.

A variety of pipettes (Table 6) and pipette tips (FIG. 3) were used to mix 20 µL of a PCR mix with 60 µL of an emulsifier-oil mixture (see Table 1). Mixing was performed by pipetting a 70 µL volume up and down 30 times. PCR cycling was performed as described in Example 3. Emulsion breaking was performed with the newly developed breaking solutions 1 and 2 (see Example 2). Subsequent hybridization was performed as described in Example 3. A comparison of the BEAMing flow cytometry data are presented in Table 7. Variations in the diameter of the pipette tip affected the emulsion formation process with larger diameters requiring additional pipetting cycles. For diameters in excess of 650 µm (FIG. 3, P250 model) the emulsion formation was only possible with a very high cycle number. Smaller diameters (FIG. 3, FXF-20 model) required fewer pipetting cycles. The shape of the pipette tip had no influence on the emulsion formation process. Electronic pipettes can have different pipetting speed settings. The speed is critical for the emulsion formation process and must be verified for each model and adjusted if necessary. If the speed is not adjustable a variation of the pipetting cycle numbers can compensate for differences in emulsion quality. However, the pipette tip-based emulsification process works for different commonly available pipette tips and pipettes. Variables that might be different between models are the size of the tip opening and the cycling speed.

TABLE 6

Pipette types

| Model | Type | Channels | Pipet Speed | Mix Volume | Mix Cycles |
|---|---|---|---|---|---|
| L-200XLS | Manual | 1 | Medium | 80 uL | 30 |
| L12-200XLS | Manual | 12 | Medium | 80 uL | 30 |
| E12-200XLS | Electronic | 12 | 6 | 80 uL | 30 |
| edp3+ LTS 200 | Electronic | 12 | 7 | 80 uL | 30 |

TABLE 7

BEAMing flow cytometry data using two different electronic pipettes for emulsion preparation

| Model | Total Single Beads | Percent Extended | Mutant Beads | Mixed Beads | Wild-type Beads | Mutant Fraction | |
|---|---|---|---|---|---|---|---|
| edp3 + LTS 200 | 723,706 | 8.57 | 6676 | 7304 | 47,696 | 10.88 | Average |
| | 44,000 | 0.86 | 750 | 1085 | 7285 | 0.62 | SD |

TABLE 7-continued

BEAMing flow cytometry data using two different electronic pipettes for emulsion preparation

| Model | Total Single Beads | Percent Extended | Mutant Beads | Mixed Beads | Wild-type Beads | Mutant Fraction | |
|---|---|---|---|---|---|---|---|
| E12-200XLS | 706,527.5 | 10.59 | 7773 | 7996 | 58,809 | 10.61 | Average |
| | 49,558 | 1.87 | 1093 | 1740 | 14,161 | 1.11 | SD |

SD—standard deviation

Example 2—Breaking Solution

The inventors used a procedure for demulsification (i.e., emulsion breaking) and subsequent recovery of the product beads (e.g., BEAMing beads) that fulfilled the following requirements: no reaction vessel (e.g., tube or 96-well plate) change, no centrifugation, no vacuum usage, no step for denaturation of double stranded DNA bound to the product beads (i.e., removal of non-bound DNA strand), and no use of non-standard pipetting. These requirements are critical for the automation and standardization of the breaking process. The approach taken was based on the screening for a solution that will allow emulsion breaking of water-in-oil emulsions and recovery of components present in the aqueous dispersed phase (e.g., product beads).

The mixing capacity of different potential emulsion breakers with water and an emulsifier-oil mixture (see Table 2) was tested. One hundred microliters of reagent 1 and 100 µL of reagent 2 (see Table 8) were mixed by pipetting up and down several times. The mixture was incubated at room temperature for 1-2 min. The mixing behavior of the aqueous and organic phases was visually inspected. 1-Propanol mixed with water and the emulsifier-oil mixture. Therefore, 1-propanol was the primary candidate reagent to mediate between the organic and aqueous phase. Only alcohols that mix with the emulsifier-oil mixture (Result: 1 phase) were subsequently tested for the ability to break emulsions (e.g., 1-methyl-1-propanol, 1-propanol, 2-Butanol) (Table 5).

TABLE 8

Potential emulsion breakers and results

| Reagent 1 | Reagent 2 | Results |
|---|---|---|
| 1-Methyl-1-Propanol | Water | 2 phases |
| 1-Methyl-1-Propanol | Emusifier - Oil Mix | 1 phase |
| 2,3-Butanediol | Water | 1 phase, |
| 2,3-Butanediol | Emusifier - Oil Mix | 2 phases, doesn't mix well |
| 1,2-Propanediol | Water | 1 phase |
| 1,2-Propanediol | Emusifier - Oil Mix | 2 phases, doesn't mix well |
| 1-Propanol | Water | 1 phase |
| 1-Propanol | Emusifier - Oil Mix | 1 phase |
| 2-Butanol | Water | 2 phases |
| 2-Butanol | Emusifier - Oil Mix | 1 phase |

Figure 4:
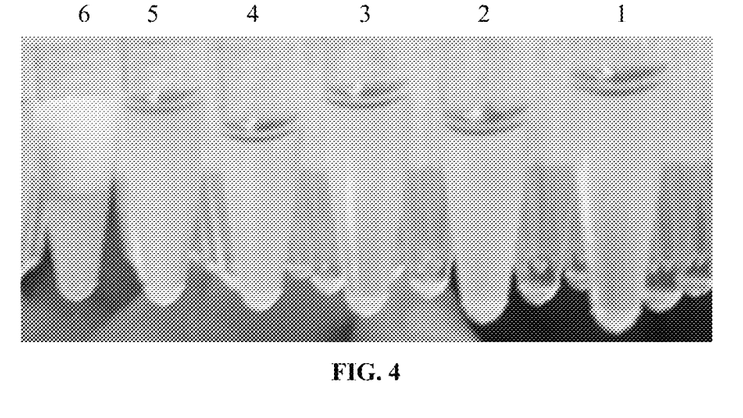
FIG. 4: Visual inspection of alcohol emulsion breakers for demulsification capacity and number of phases.

Different alcohols were tested for the ability to break emulsions be evaluating the ability to result in a single homogeneous phase. Eighty microliter emulsions were prepared using Dynabeads® MyOne™ Streptavidin C1 (Life Technologies) coated with 5'-2-Bio-TTCCCGCGAAAT-TAATACGAC (SEQ ID NO: 1) bead-adapter sequence and 1×PCR buffer (67 mM Tris (pH 8.8), 16.6 mM $(NH_4)_2SO_4$, 6.7 mM $MgCl_2$) and mixed with breaking solutions (see Table 8) by pipetting up and down several times. The mixtures were incubated for 1-2 min and visually inspected for demulsification capacity and number of phases (Table 9; FIG. 4). 2-Methyl-1-propanol and 2-butanol were strong emulsion breakers and resulted in one clear phase (i.e., no separation of the dispersed and continuous phases). Pure alcohol (approx. 100%) resulted in clumping of product beads on the vessel wall and could not be combined with sodium hydroxide for denaturation of bead bound DNA due to bead clumping. Therefore, breaking solution should contain components that prevent bead clumping, as well as be compatible with sodium hydroxide.

TABLE 9

Alcohol emulsion breakers and results

| No. | Breaking Solution | Volume Reagent 1 | Volume Emulsion PCR | Visual Result |
|---|---|---|---|---|
| 1 | 2-Methyl-1-Propanol | 150 µL | 80 µL | Demulsification +++; clear; 1 phase |
| 2 | 2-Methyl-1-Propanol | 100 µL | 80 µL | Demulsification +; cloudy; 1 phase |
| 3 | 2-Butanol | 150 µL | 80 µL | Demulsification +++; clear; 1 phase |
| 4 | 2-Butanol | 100 µL | 80 µL | Demulsification ++; cloudy; 1 phase |
| 5 | 1-Propanol | 150 µL | 80 µL | Demulsification +; cloudy; 1 phase |
| 6 | 1-Propanol | 100 µL | 80 µL | Demulsification +; cloudy; 2 phases |

Based on these results, optimization of the emulsion breaker was performed. Eighty microliter emulsions were prepared using Dynabeads® MyOne™ Streptavidin C1 (Life Technologies) coated with 5'-2-Bio-TTCCCGC-GAAATTAATACGAC (SEQ ID NO: 1) bead-adapter sequence and 1×PCR buffer (67 mM Tris (pH 8.8), 16.6 mM $(NH_4)_2SO_4$, 6.7 mM $MgCl_2$) and mixed with 100 µL breaking solution (see Table 10) by pipetting up and down about 10 times. The mixtures were incubated for 1-2 min and visually inspected for demulsification capacity and number of phases (Table 10). There was no clear correlation between the concentration of NX-SDS (100 mM NaCl, 1% Triton X-100, 10 mM Tris HCl (pH 7.5), 1 mM EDTA, 1% SDS; see U.S. Patent Publn. 20100190153, incorporated herein by reference) or the alcohols with the appearance of a cloudy (white) viscous supernatant or the clumping of product beads. The ratio between alcohol 1 and 2 also showed no clear correlation with the cloudy (white) viscous supernatant or the clumping of product beads. The ratio between the alcohols and the NX-SDS also showed no clear correlation with the cloudy (white) viscous supernatant or the clumping of product beads. Two solutions showed the overall best performance: Solution 1 (ID4) and Solution 6 (ID8).

TABLE 10

Optimization of emulsion breaker and results

| No. | Reagent | Results |
|---|---|---|
| 1 (ID4) | 20% NX-SDS 40% 2-Butanol 40% 1-Propanol | 3 phases; beads in oil; rating good |
| 2 (ID5) | 40% NX-SDS 30% 2-Butanol 30% 1-Propanol | 2 phases, H2O phase small; some bead clumping |
| 3 (ID6) | 20% NX-SDS 40% 2-Butanol 40% 1-Propanol | 2 phases, oil phase viscous white; rating bad |
| 4 | 33% NX-SDS 33% 2-Butanol 33% 1-Propanol | 3 phases, some bead clumping; rating average |
| 5 (ID7) | 40% NX-SDS 20% 2-Butanol 40% 1-Propanol | 2 phases, oil phase viscous white; rating bad |
| 6 (ID8) | 30% NX-SDS 40% 2-Butanol 30% 1-Propanol | 2 phases, oil phase viscous white; rating average to good |
| 7 (ID9) | 25% NX-SDS 50% 2-Butanol 25% 1-Propanol | 2 phases, water phase small; bead clumping; beads in oil |
| 8 (ID10) | 40% NX-SDS 40% 2-Butanol 20% 1-Propanol | 2 phases, beads in water phase, beads clump afterwards when beads are washed afterwards with PBS |
| 9 (ID11) | 30% NX-SDS 30% 2-Butanol 40% 1-Propanol | 2 phases, beads in water phase, beads clump afterwards when beads are washed afterwards with PBS; better than No. 8 |
| 10 (ID12) | 25% NX-SDS 25% 2-Butanol 50% 1-Propanol | 2 phases, bead clumping |

Following the same procedure, further adaption of the breaking solution ratios was performed based on Solutions 1 and 6 (Table 11).

TABLE 11

Further optimization of emulsion breaker and results

| No. | Reagent | Results |
|---|---|---|
| 1 (ID4) | 20% NX-SDS 40% 2-Butanol 40% 1-Propanol | See Table 10 |
| 6 (ID8) | 30% NX-SDS 40% 2-Butanol 30% 1-Propanol | See Table 10 |
| 11 (ID21) | 25% NX-SDS 40% 2-Butanol 35% 1-Propanol | 2 phases, water phase small; good |

A second emulsion breaking solution containing sodium hydroxide was developed for emulsion clean-up and denaturation of bead-bound DNA. Eighty microliter emulsions were prepared using Dynabeads® MyOne™ Streptavidin C1 (Life Technologies) coated with 5'-2-Bio-TTCCCGC-GAAATTAATACGAC (SEQ ID NO: 1) bead-adapter sequence and 1×PCR buffer (67 mM Tris (pH 8.8), 16.6 mM (NH$_4$)$_2$SO$_4$, 6.7 mM MgCl$_2$) and mixed with 100 µL breaking solution 11 (ID21) by pipetting up and down about 10 times. The mixtures were placed on a magnet for 1-2 min and the breaking solution-emulsion mixture was removed. After removing the 96-well plate from the magnet, 100 µL emulsion breaker with NaOH was added and mixed by pipetting. The mixtures were visually inspected both before and after being placed on a magnet for 1-2 min (Table 12).

TABLE 12

Development of emulsion breaker with NaOH

| No. | Reagent | Results; Bead resuspension |
|---|---|---|
| 1 (ID13) | 60% NX-SDS NaOH 20% 2-Butanol 20% 1-Propanol | difficult |
| 2 (ID14) | 70% NX-SDS NaOH 15% 2-Butanol 15% 1-Propanol | good; removal of remaining oil possible |
| 3 (ID15) | 80% NX-SDS NaOH 10% 2-Butanol 10% 1-Propanol | very good; removal of remaining oil possible |
| 4 (ID16) | 90% NXSDS NaOH 5% Butan2ol 5% 1-Propanol | good; |
| 5 (ID17) | 60% NXSDS NaOH 40% 1-Propanol | not possible |
| 6 (ID18) | 70% NXSDS NaOH 30% 1-Propanol | not possible |
| 7 (ID19) | 80% NXSDS NaOH 20% 1-Propanol | not possible |
| 8 (ID20) | 90% NXSDS NaOH 10% 1-Propanol | not possible |

A two-step breaking process was developed using emulsion breakers 1 and 2 (see Tables 2 and 3). Emulsion breaker 1 allows efficient emulsion breaking Product beads can be resuspended (i.e., no bead clumping) when using emulsion breaker 1. Emulsion breaker 2 (an emulsion clean-up solution) can be used to remove additional emulsifier-oil residues and to denature bead-bound DNA when required for downstream applications. Emulsion breaker 2 can denature and wash product beads without bead clumping. The procedure requires no plate/tube change, no usage of a vacuum manifold to remove emulsifier-oil mixture after magnetic separation, and no centrifugation. Additionally, the procedure is completely based on standard pipetting steps and can be performed by automated liquid handling systems.

Example 3—Precision Test

Figure 5:
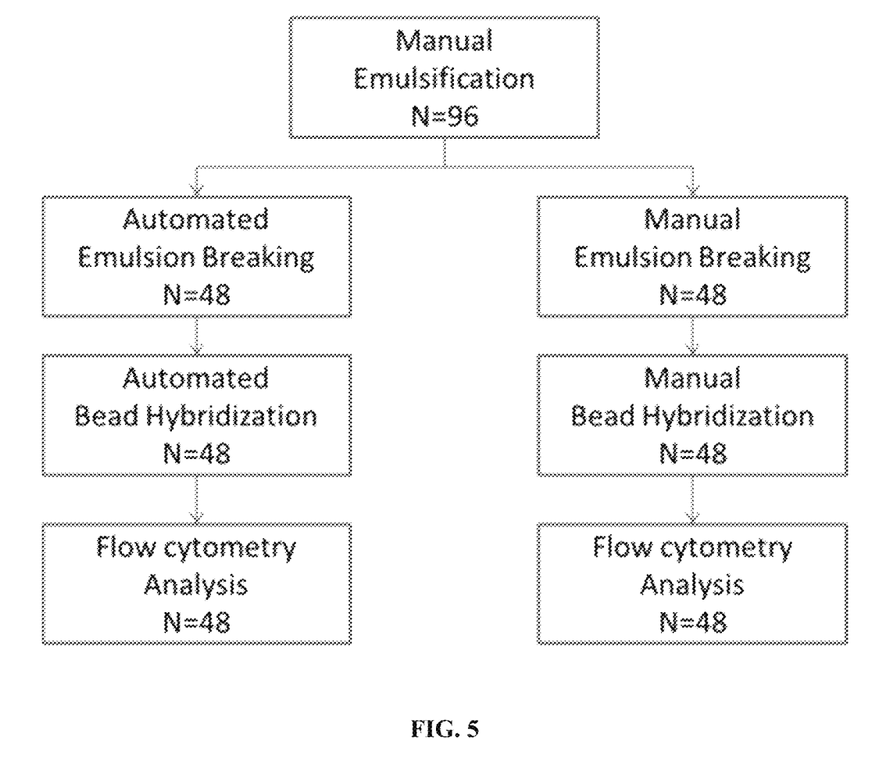
FIG. 5: Setup of the within-run precision test of the emulsification and emulsification breaking processes (automated and manual).

The setup of the within-run precision test of the emulsification and emulsification breaking processes (automated and manual) is shown in FIG. 8. To prepare the emulsion PCR beads, one milliliter of Dynabeads MyOne Streptavidin C1 (Life Technologies) were thoroughly resuspended in a 1.5 mL microcentrifuge tube by vortexing. After a brief centrifugation, the tube was placed on a Dynal MPC magnetic particle concentrator (Life Technologies) for 1 min to concentrate the beads, and the supernatant was removed with a pipette. The beads were washed twice with 1000 µL 1× binding wash buffer (200 mM Tris-HCl (pH 8.4), 500 mM KCl) and resuspended by vortexing. After each wash and a brief centrifugation, the tube was placed on the Dynal magnet for 1 min to concentrate the beads and the supernatant was removed with a pipette. The beads were resuspended in 1000 µL 1× binding buffer (1 M NaCl, 5 mM Tris-HCl (pH 7.5), 0.5 mM EDTA), 100 µL of biotinylated bead-adaptor primer (100 µM in 1×TE buffer; 5'-2-Bio-TTCCCGCGAAATTAATACGAC (SEQ ID NO: 1); IDT) was added, and the mixture was vortexed immediately. The bead suspension was incubated at 15-25° C. for 15 min. After a brief centrifugation, the tube was placed on the Dynal MPC magnetic particle concentrator for 1 min to concentrate the beads and the supernatant was removed with a pipette. The beads were washed twice with 1000 µL 1× binding wash buffer (200 mM Tris-HCl (pH 8.4), 500 mM KCl) and finally resuspended in 1000 µL 1× binding wash buffer.

For emulsion PCR, the emulsifier-oil mixture was vigorously shaken before use for at least 30 s and then let sit for 15-30 min or until the bubbles disappeared. The DNA template was prepared with bead-tag and solution-tag at a concentration of 35 pg/µL in TE buffer or water. The emulsion PCR reaction was prepared in a 96-well plate (Thermo-Fast® 96 PCR Plates; Abgene/Thermo Scientific) by mixing the following: 15 µL emulsion PCR master mix (1.56×PCR buffer (10×PCR buffer: 670 mM Tris (pH 8.8), 166 mM $(NH_4)_2SO_4$, 67 mM $MgCl_2$), 7.82 mM $MgCl_2$, 0.78 mM dNTPs, 78.2 nM bead-tag 5'-TTCCCGCGAAAT-TAATACGAC (SEQ ID NO 1), 12.5 µM solution-tag 5'-gctggagctctgcagcta), 0.8 µL emulsion PCR beads, 1 µL peqGOLD Taq DNA polymerase (5 U/µL; Peqlab), and 5 µL diluted DNA template (PCR product mixture comprised of KRAS wild-type and mutant sequence with bead-tag and solution-tag. 5'-KRAS wild-type sequence: gctggagctctgca-gctaTGACTGAATATAAACTTGTGGTAGTTGGAGCTG-GTGGCGTAGGCA AGAGTGCCTTGACGATACA-GCTAATTCAGAATCATTTTGTGGACGAATATGgtcgtattaat ttcgcggga (SEQ ID NO: 2). Seventy microliters of the emulsifier-oil mixture (see Table 1) was added using an electronic multichannel pipette and mixed by pipetting a volume of 80 µL up and down 30 times. The plates were sealed with adhesive PCR film (Abgene/Thermo Scientific) and run according to the PCR program in Table 13.

TABLE 13

Emulsion PCR program

| Step | Temp. [° C.] | Time [mm:ss] | Back to step | No. of runs |
|------|--------------|--------------|--------------|-------------|
| 1    | 94           | 02:00        |              | 1           |
| 2    | 94           | 00:10        |              | 3           |
| 3    | 68           | 00:50        |              | 3           |
| 4    | 70           | 01:20        | 2            | 3           |
| 5    | 94           | 00:10        |              | 3           |
| 6    | 65           | 00:50        |              | 3           |
| 7    | 70           | 01:20        | 5            | 3           |
| 8    | 94           | 00:10        |              | 3           |
| 9    | 62           | 00:50        |              | 3           |
| 10   | 70           | 01:20        | 8            | 3           |
| 11   | 94           | 00:10        |              | 50          |
| 12   | 59           | 00:50        |              | 50          |
| 13   | 70           | 01:20        | 11           | 50          |
| 14   | 70           | 02:00        |              | 1           |

Manual emulsion breaking was performed by adding 100 µL breaking solution 1 (see Table 2) to each emulsion PCR reaction and pipetted up and down 10 times. The 96-well plate was placed on a 96-well magnet (SPRI 96 well ring super magnet plate; Beckman Coulter) for 1 min after which the supernatant was disposed of completely. The plate was removed from the magnet and 100 µL breaking solution 1 was added to each well and pipetted up and down 10 times. The 96-well plate was placed on a 96-well magnet for 2.5 min after which the supernatant was disposed of completely. The plate was removed from the magnet and 100 µL breaking solution 2 (see Table 3) was added to each well, pipetted up and down 10 times, and incubated at room temperature for 2 min. The 96-well plate was placed on a 96-well magnet for 1 min after which the supernatant was disposed of completely. The plate was removed from the magnet and 100 µL probe mix (3 M TMAC, 100 mM Tris-HCl (pH 7.5), 4 mM EDTA, 16.7 µM of universal [KRAS Ex1, 5'-DY510XL-tgacgatacagctaattca], mutant [KRAS Ex1 34G>A, 5'-Cy5-ggagctagtggcgt], and wild-type [KRAS Ext, 5'-FAM-aggagctggtggcgta] probe) was added to each well and pipetted up and down 10 times. The plates were sealed with adhesive PCR film and placed in the thermal cycler (Sensoquest), which was run according to the following program for allele specific hybridization: 30 sec at 70° C., ramp to 24° C. by 0.05° C./s, and 1 min at 24° C. Then the plate was placed on a magnet for 1 min and carefully unsealed. Eighty microliters of the supernatant was removed. The plate was removed from the magnet, and 80 µL of 1×PBS (Dulbecco's) was added to each well and pipetted up and down 10 times. This washing procedure was repeated twice more with the final resuspension being in 160 µL 1×PBS.

The procedure for automated breaking was implemented on a Biomek NK with a 96-well head (Beckman Coulter) using FX-250-R and FX-50-R robotic tips (Beckman FX; Axygen).

Flow cytometry was performed using an Accuri C6 flow cytometer (Becton Dickinson) that was prepared according to the manufacturer's instructions. The beads were resuspended in the 96-well plate and run according to the conditions in Table 14. FCS expression v3 software (DeNovo) was used to analyze the FCS files. Analysis was performed on single bead populations. The results of the precision test are presented in Table 15.

TABLE 14

Flow cytometry conditions

| Option | Value |
|--------|-------|
| Plate Type | 96-well Plate |
| Run Limits | 130 µL |
| Wash Settings | 3 Cycles |
| Fluidics | Fast |
| Agitate Plate | None |

TABLE 15

Precision test results

| | | Emulsion PCR, Breaking, and Hybridization | |
|---|---|---|---|
| Measurement | Parameter | Automated | Manual |
| Total Single Beads | (N) | 48 | 48 |
| | Average | 688,873 | 700,083 |
| | Standard deviation | 42,018 | 27,319 |
| | Relative standard deviation | 6.1% | 3.9% |
| Extended Beads | Average | 15.97 | 16.60 |
| | Standard deviation | 2.74 | 3.05 |
| | Relative standard deviation | 17.2% | 18.4% |
| Mutant Fraction | Average | 0.1554 | 0.1760 |
| | Standard deviation | 0.0187 | 0.0234 |
| | Relative standard deviation | 12.0% | 13.3% |
| | Median | 0.1550 | 0.1740 |
| | Min | 0.1192 | 0.1181 |
| | Max | 0.2060 | 0.2335 |

Figure 6:
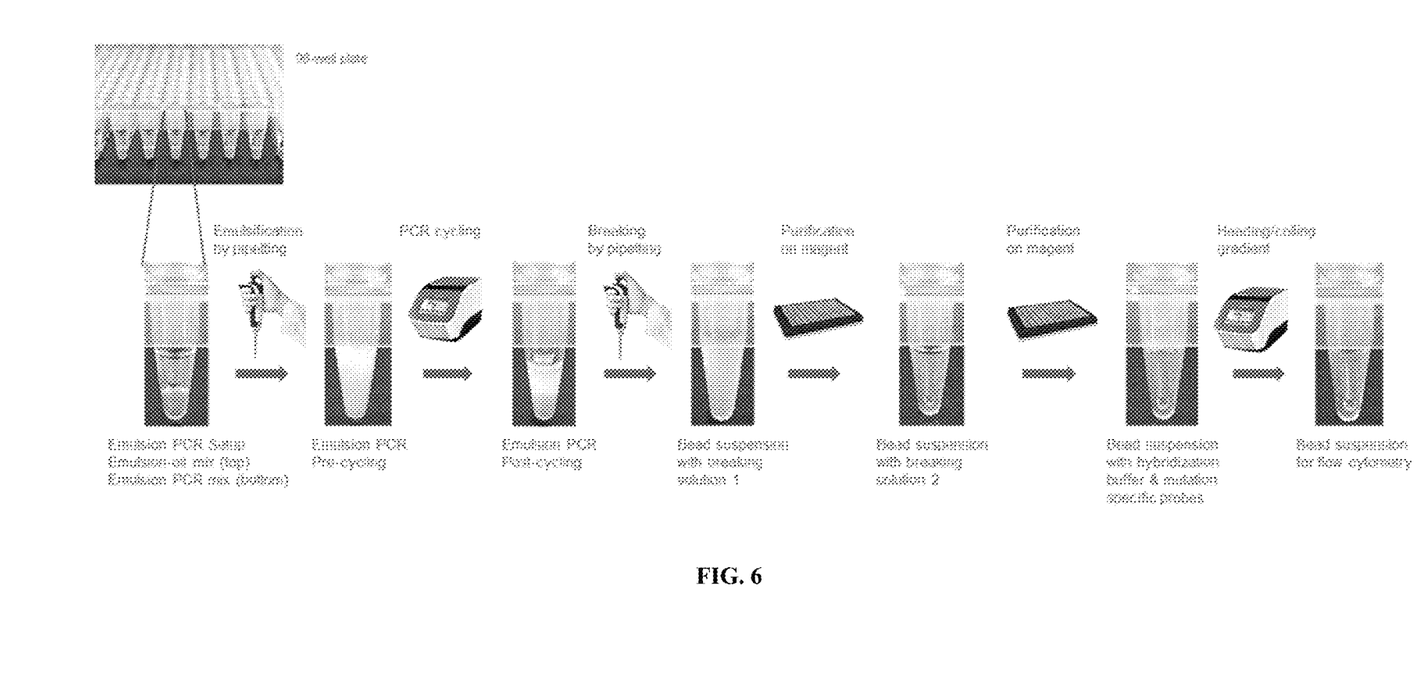
FIG. 6: Steps of an example emulsification and emulsion breaking process of the embodiments.

The described emulsification and emulsion breaking processes (see FIG. 6) can be used for the BEAMing procedure. In particular, a mutation can be quantified with an overall standard deviation of 12% and 13% based on automated and manual emulsion breaking processes, respectively.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Publn. 20100041048
U.S. Patent Publn. 20100190153
U.S. Patent Publn. 20110201526
U.S. Patent Publn. 20120088684
Diehl et al., Detection and quantification of mutations in the plasma of patients with colorectal tumors. *Proc. Natl. Acad. Sci. USA*, 102(45):16368-16373, 2005.
Diehl et al., BEAMing: single-molecule PCR on microparticles in water-in-oil emulsions. *Nat. Methods*, 3(7):551-9, 2006.
Diehl et al., Circulating mutant DNA to assess tumor dynamics. *Nature Medicine*, 14(9):985-90, 2008.
Diehl et al., Analysis of mutations in DNA isolated from plasma and stool of colorectal cancer patients. *Gastroenterology* 135(2):489-98, 2008.
Dressman et al., Transforming single DNA molecules into fluorescent magnetic particles for detection and enumeration of genetic variations. *Proc. Natl. Acad. Sci. USA* 100:8817-8822, 2003.
Li et al., BEAMing up for detection and quantification of rare sequence variants. *Nat Methods* 3:95-97, 2006.
Mitra et al., Fluorescent in situ sequencing on polymerase colonies. *Anal. Biochem.* 320:55-65, 2003
Ronaghi et al., Analyses of secondary structures in DNA by pyrosequencing. *Anal. Biochem.* 267: 65-71, 1999

What is claimed is:

1. A method for emulsion polymerase amplification comprising:
   (a) providing a mixture comprising an aqueous phase comprising polymerase reaction mixture and an oil mixture;
   (b) emulsifying the mixture by passing the mixture through an orifice having a diameter between 2 mm and 50 μm with a velocity of 40 μl/s to 220 μl/s; and
   (c) subjecting the emulsion to nucleic acid amplification;
   wherein the oil mixture comprises mineral oil, diethylhexyl carbonate, polyglyceryl-4 isostearate, cetyl PEG/PPG-10/1-dimethicone, and hexyl laurate.

2. The method of claim 1, wherein the mixture is passed through the orifice at least 5 times.

3. The method of claim 1, wherein the mixture is passed through the orifice with a velocity of 60 μl/s to 180 μl/s.

4. The method of claim 1, wherein the orifice has a diameter of between 1 mm and 100 μm.

5. The method of claim 1, wherein the oil mixture comprises:
   (a) 10-30% (w/v) mineral oil;
   (b) 55-75% (w/v) diethylhexyl carbonate;
   (c) 5-15% (w/v) of a composition comprising polyglyceryl-4 isostearate; cetyl PEG/PPG-10/1-dimethicone; and hexyl laurate; and
   (d) 5-15% (w/v) of polyglyceryl-3-oleate or polyglyceryl-4 isostearate.

6. The method of claim 1, further defined as a method for emulsion polymerase amplification in a plurality of reaction vessels.

7. The method of claim 6, wherein the plurality of reaction vessels are arrayed as wells on a plate.

8. The method of claim 1, wherein the aqueous phase comprises a plurality beads conjugated to a plurality of nucleic acid templates.

9. The method of claim 8, wherein the beads are magnetic.

10. The method of claim 1, further comprising:
    (d) adding a breaking solution to the mixture to break the emulsion.

11. The method of claim 10, wherein the breaking solution comprises:
    (a) 20-50% 2-butanol;
    (b) 20-50% 1-propanol; and
    (c) 10-40% of water.

12. The method of claim 10, wherein the breaking solution further comprises 0.1% to 2.0% SDS.

13. The method of claim 10, wherein the breaking solution comprises:
    (a) 30-50% 2-butanol;
    (b) 30-50% 1-propanol; and
    (c) 10-30% of water.

14. The method of claim 10, wherein the breaking solution comprises an alkaline denaturing agent.

15. The method of claim 10, further comprising:
    (e) removing the oil or aqueous phase.

16. The method according to claim 1, wherein the oil mixture further comprises polyglyceryl-3-oleate.

17. The method of claim 1, wherein passing the mixture through an orifice comprises pipetting the mixture.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
ttcccgcgaa attaatacga c                                              21

<210> SEQ ID NO 2
<211> LENGTH: 134
<212> TYPE: DNA
<213> ORGANISM: Artificial Sequence
<220> FEATURE:
<223> OTHER INFORMATION: Synthetic primer

<400> SEQUENCE: 2
gctggagctc tgcagctatg actgaatata aacttgtggt agttggagct ggtggcgtag    60
gcaagagtgc cttgacgata cagctaattc agaatcattt tgtggacgaa tatggtcgta   120
ttaatttcgc ggga                                                    134
```